United States Patent
Pickett et al.

[11] Patent Number: 5,856,486
[45] Date of Patent: Jan. 5, 1999

[54] POLYCARBONATE COMPOSITIONS COMPRISING HINDERED AMINE LIGHT STABILIZERS

[75] Inventors: James Edward Pickett, Niskayuna; Randall Lee Carter, Clifton Park, both of N.Y.; Gary Eugene Spilman, Evansville, Ind.

[73] Assignee: General Electric Company, Schenectady, N.Y.

[21] Appl. No.: 924,413

[22] Filed: Aug. 27, 1997

[51] Int. Cl.⁶ .................................................. C07D 241/04
[52] U.S. Cl. ........................... 544/385; 544/349; 544/357
[58] Field of Search ................... 544/385, 357, 544/349

[56] References Cited

U.S. PATENT DOCUMENTS

| | | | |
|---|---|---|---|
| 3,919,234 | 11/1975 | Ramey et al. | 544/385 |
| 3,920,659 | 11/1975 | Ramey et al. | 544/385 |
| 4,190,571 | 2/1980 | Lai et al. | 544/357 |
| 4,208,522 | 6/1980 | Ramey et al. | 544/385 |
| 4,292,240 | 9/1981 | Lai et al. | 544/349 |
| 4,480,092 | 10/1984 | Lai et al. | 528/423 |
| 4,525,504 | 6/1985 | Morris et al. | 524/99 |
| 5,071,981 | 12/1991 | Son et al. | 544/198 |

*Primary Examiner*—Terressa Mosley
*Attorney, Agent, or Firm*—Noreen C. Johnson; Douglas E. Stoner

[57] ABSTRACT

The instant invention relates to weatherable polycarbonate compositions (formulations or blends) comprising piperazinone or piperazine dione based HALS. These piperazinone or piperazine dione based HALS impart photostability to the polycarbonate formulations, thereby reducing yellowing or other forms of light induced degradation.

12 Claims, No Drawings

POLYCARBONATE COMPOSITIONS COMPRISING HINDERED AMINE LIGHT STABILIZERS

FIELD OF INVENTION

The instant invention relates to weatherable compositions (blends and formulations) comprising polycarbonate and hindered amines light stabilizers.

BACKGROUND OF THE INVENTION

Formulations and blends comprising polycarbonates are known to degrade upon prolonged exposure to sun light or other forms of light. One of the effects observed is yellowing of the polycarbonate blend/formulation. This problem has been alleviated by the use of light absorbers or light blockers in the polycarbonate blends. Thus ultraviolet light absorbers (UVA) are known to be used in polycarbonate formulations to protect these formulations from degradation due to exposure to different forms of light.

Use of Hindered Amine Light Stabilizers (HALS) to stabilize polyolefins has been known. Commercially used HALS have been based mainly on 2,2,6,6-tetramethyl piperidine, except for those based on piperazinones. U.S. Pat. Nos. 4,190,571; 4,292,240; 4,480,092; and 5,071,981 disclose some of the piperazinone based HALS, while U.S. Pat. Nos. 3,919,234; 3,920,659 and 4,208,522 disclose some of the piperazine dione based HALS.

The use of HALS in polycarbonates is not very common. The stabilizing effect of HALS on polycarbonate formulations/blends has been described as "minor", see for example Thompson and Klemchuk in Polymer Durability, R. L. Clough et al., ACS Advances in Chemistry 249, 1995, pp 303–317. The use of UVA in polycarbonate formulations has provided a way to retard the rate of degradation of polycarbonates as a result of exposure to light. This method how ever does not offer a complete protection of polycarbonate formulations from light induced degradation or discoloration. There is thus a continued need for a method or formulation that will help protect polycarbonate based formulations/blends from degradation or discoloration due to exposure to light.

It has been surprisingly found that use of the piperazinone and piperazine dione based HALS, contrary to studies reported above, in compositions comprising polycarbonate significantly increases the photostability thereby slowing the degradation of the polycarbonate compositions. It has also been surprisingly found that the HALS can be combined with polycarbonates without any significant chemical reaction between the two and with the least effect on melt stability of the polycarbonate compositions.

SUMMARY OF THE INVENTION

The instant invention provides a composition comprising a polycarbonate, and at least one of a piperazinone or a piperazine dione based HALS. Incorporation of the piperazinone or piperazine dione based HALS in the polycarbonate composition surprisingly renders weatherable polycarbonate compositions and protects the polycarbonate compositions from the undesired degradation or discoloration due to exposure to light.

DETAILED DESCRIPTION OF THE INVENTION

The present invention provides a composition comprising, a polycarbonate, and at least one of a piperazinone and piperazine dione based HALS. Another embodiment of the invention provides a composition wherein, (a) the polycarbonate comprises from about 95% to about 99.95% by weight of the total composition; and (b) the piperazinone or piperazine dione based HALS comprises from about 5% to about 0.05% by weight of the total composition. In a further preferred embodiment is provided a composition wherein the piperazinone or piperazine dione based HALS comprises from about 0.1% to about 1% by weight of the total composition.

A second aspect of the instant invention provides a composition comprising, (a) a polycarbonate; (b) at least one of the piperazinone or piperazine dione based HALS; (c) additives; and (d) a blend stock. In one of its embodiment is provided a composition wherein: (a) the polycarbonate comprises from about 10% to about 99.9% by weight of the total composition; (b) the piperazinone or piperazine dione based HALS comprises from about 0.05% to about 5% by weight of the total composition; (c) additives comprise from about 0.01% to about 25% by weight of the total composition; and (d) the blend stock comprises from about 0% to about 89% by weight of the total composition.

Preferred embodiments provide a composition wherein HALS comprise from 0.1% to 1%, and the blend stock comprises from 30% to 60% by weight of the total composition. In yet another preferred embodiment is provided a composition wherein the polycarbonate is BPA polycarbonate.

Another preferred embodiment provides a composition wherein the piperazinone or piperazine dione based HALS is selected from:

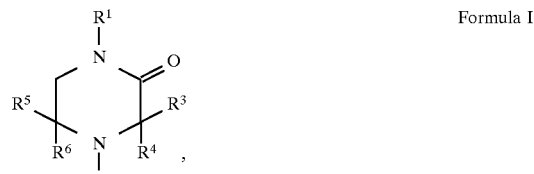

Formula I

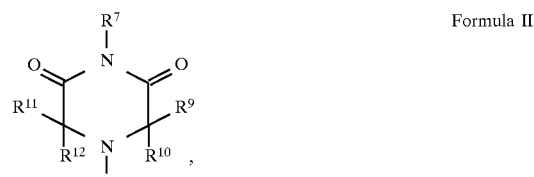

Formula II

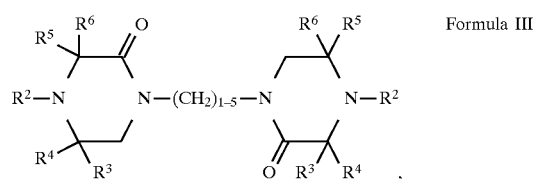

Formula III and

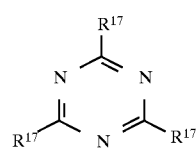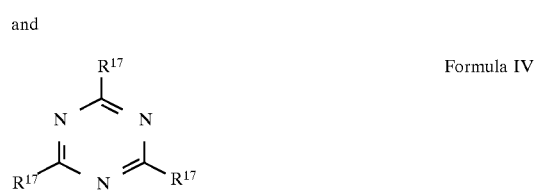

Formula IV wherein:

$R^1$ and $R^2$ are independently $C_{1-24}$ alkyl, hydrogen, acyl, benzyl, $C_{1-12}$ haloalkyl,, $C_{2-14}$ alkenyl, unsubstituted $C_{7-14}$ aralkyl, or carboalkoxy; $R^2$ optionally also represents oxygen;

$R^3$ and $R^4$ independently represent $C_{1-18}$ haloalkyl, $C_{1-18}$ alkyl, $C_{5-18}$ cycloalkyl, $C_{2-18}$ alkenyl, or unsubstituted $C_{7-18}$ aralkyl; or $R^3$ and $R^4$, when taken together with the carbon to which they are attached, form a $C_{4-12}$ alicyclic ring;

$R^5$ and $R^6$ are independently $C_{1-18}$ haloalkyl, $C_{1-18}$ alkyl, $C_{2-18}$ alkenyl, or unsubstituted $C_{7-18}$ aralkyl; or $R^5$ and $R^6$ when taken together with the carbon atom to which they are attached, form a $C_{4-12}$ alicyclic ring;

$R^7$ is $C_{1-20}$ alkyl, benzyl,

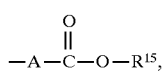

or

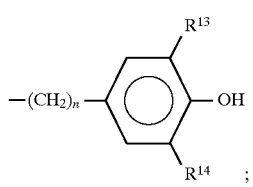

$R^8$ is hydrogen, $C_{1-24}$ alkyl, or aryl;

$R^9$ and $R^{10}$ independently represent $C_{1-18}$ haloalkyl, $C_{1-18}$ alkyl, $C_{5-18}$ cycloalkyl, $C_{2-18}$ alkenyl, or unsubstituted $C_{7-18}$ aralkyl; or $R^9$ and $R^{10}$, when taken together with the carbon to which they are attached, form a $C_{4-12}$ alicyclic ring;

$R^{11}$ and $R^{12}$ are independently $C_{1-18}$ haloalkyl, $C_{1-18}$ alkyl, $C_{2-18}$ alkenyl, or unsubstituted $C_{7-18}$ araalkyl; or $R^{11}$ and $R^{12}$ when taken together with the carbon atom to which they are attached, form a $C_{4-12}$ alicyclic ring;

$R^{13}$ and $R^{14}$ are independently $C_{1-8}$ alkyl, wherein at least one of said groups is branched on the $\alpha$ carbon atom; $R^{15}$ is $C_{1-20}$ alkyl; $R^{17}$ is

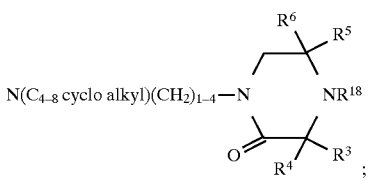

$R^{18}$ is H or $C_{1-4}$ alkyl;

A is a straight or branched chain (lower) alkylene having from 1 to 6 carbon atoms optionally substituted with $C_1$–$C_6$ alkyl; and n represents an integer from 1 to 4.

Preferred HALS are represented by:

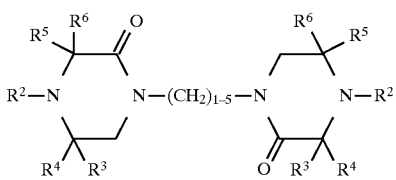

and

Formula III

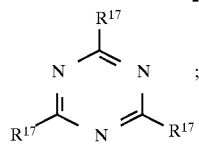

Formula IV wherein, $R^3$, $R^4$, $R^5$, and $R^6$ are each methyl; $R^{17}$ is

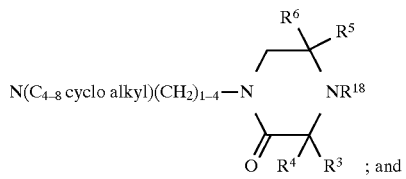

$R^{18}$ is H or $C_{1-4}$ alkyl. A further preferred embodiment provides a composition wherein the HALS is a piperazine dione represented by

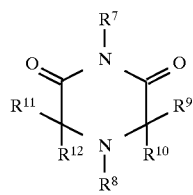

Formula II wherein, $R^9$ and $R^{10}$ independently represent methyl; or $R^9$ and $R^{10}$, when taken together with the carbon to which they are attached, form a cyclohexyl ring; and $R^{11}$ and $R^{12}$ independently methyl; or $R^{11}$ and $R^{12}$, when taken together with the carbon atom to which they are attached, form a cyclohexyl ring.

As used in the instant invention a polycarbonate comprises multiple structural units represented by the formula $$[-O-A^1-O-C(O)-]$$ Formula V wherein $A^1$ is a divalent aromatic hydrocarbon radical. Suitable $A^1$ radicals include m-phenylene, p-phenylene, 4,4'-biphenylene, 4,4'-bi(3,5-dimethyl)phenylene, 2,2-bis(4-phenylene)propane and similar radicals such as those which correspond to the dihydroxy-substituted aromatic hydrocarbons disclosed by name or formula (generic or specific) in U.S. Pat. No. 4,217,438.

The $A^1$ radical preferably has the formula $$-A^2-Y-A^3-$$ Formula VI wherein each of $A^2$ and $A^3$ is a mono cyclic divalent aromatic hydrocarbon radical and Y is a bridging hydrocarbon radical in which one or two atoms separate $A^2$ from $A^3$. The free valence bonds in formula VI are usually in the meta or para positions of $A^2$ and $A^3$ in relation to Y. Compounds in which $A^1$ has formula VI are bisphenols, and for the sake of brevity the term "bisphenol" is sometimes used herein to designate the dihydroxy-substituted aromatic hydrocarbons; it should be understood, however, that non-bisphenol compounds of this type may also be employed as appropriate.

In formula VI, the $A^2$ and $A^3$ values may be unsubstituted phenylene or hydrocarbon-substituted derivatives thereof, illustrative substituents (one or more) being alkyl and alkenyl. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. Illustrative radicals of this type are methylene, cyclohexylmethylene, 2-[2.2.1]-bicycloheptylmethylene, ethylene, isopropylidene, neopentylidene, cyclohexylidene, cyclopentadecylidene, cyclododecylidene and adamantylidene; gem-alkylene (alkylidene) radicals are preferred. Also included, however, are unsaturated radicals. For reasons of availability and particular suitability for the purposes of this invention, the preferred bisphenol is 2,2-bis(4-hydroxyphenyl)propane ("BPA"), in which Y is isopropylidene and $A^2$ and $A^3$ are each p-phenylene. A detailed description of polycarbonates used in the instant invention is described in U.S. Pat. Nos. 4,125,572; 3,028,365; 3,334,154 and 3,915,926, all of which are incorporated herein by reference.

The compositions of the instant invention comprise at least one piperazinone or piperazine dione based HALS. It should be noted that one or a mixture of more than one piperazinone or piperazine dione based HALS can be used as part of the instantly claimed compositions. The piperazinone or piperazine dione based HALS are generally represented by Formula I, Formula II, Formula III, or Formula IV. Also as used herein, additives include such materials as colorants, whitening agents, thermal stabilizers, metal deactivators, impact modifiers, extenders, antistatic agents, and processing aids. The different additives that can be incorporated in the compositions of the instant invention are commonly used and known to one skilled in the art. Illustrative descriptions of such additives may be found in R. Gachter and H. Muller; Plastics Additives, $4^{th}$ edition, 1993 and are incorporated herein by reference.

Also, as used in the instant invention, the phrase blend stock is used to describe one or more polymeric ingredients represented by aromatic polyesters, aliphatic polyesters, and styrenic polymers. Examples of blend stocks include poly (4-butylene terephthalate, poly(ethylene terephthalate), acrylonitrile-butadiene-styrene copolymer (ABS), styrene-acrylonitrile copolymer (SAN), styrene-acrylonitrile-acrylate copolymers (ASA), and poly(1,4-cyclohexanedimethanol-1,4-cyclohexanedicarboxylate) (PCCD).

EXPERIMENTAL DETAILS

The examples illustrate the instant invention by providing data that deals with the weathering performance of the piperazinone based HALS in polycarbonate.

EXAMPLE 1

Photostability of Solvent-Cast Films

BPA polycarbonate films, approximately 18 microns thick, were cast from methylene chloride by drawing 20% solids solutions on a glass plate using a 6 mil doctor blade. HALS was added to methylene chloride solution at 1.0% by weight of polycarbonate resin.

These films were exposed in an Atlas Ci35a xenon arc Weather-Ometer® equipped with CIRA inner and soda lime outer filters. The light cycle was 165 minutes long at an irradiance of 0.77 W/m$^2$ at 340 nm, black panel temperature 50 C., dry bulb temperature 30 C., and wet bulb depression 7° C. There was a 15 minute dark cycle with water spray during the last 10 minutes. Exposure is measured in total kilojoules (kJ) of irradiance at 340 nm.

The Yellowness Index (YI, obtained by ASTM procedure D-1925) of the films is shown in Table 1. A lower YI number suggests lesser effect of light on the polycarbonate and thereby higher photostability.

The structures of the HALS are shown in FIG. 2. bis[2,2,6,6-tetramethyl-4-piperidinyl]sebacate (Tinuvin® 770), bis[1,2,2,6,6-pentamethyl-4-piperidinyl] sebacate (Tinuvin® 765), and 1-acetyl-4-(3-dodecyl-2,5-dioxo-1-pyrrolidinyl)-2,2,6,6-tetramethylpiperidine (Sanduvor® 3058) are commercial HALS all of the piperidine class. 1,1'-(1,2-ethanediyl) bis[3,3,5,5-tetramethylperazinone] (Good-rite™ 3034, GR3034 for short) is a representative of the piperazinone class. The YI data shows that GR 3034 is superior in reducing the photo yellowing of cast polycarbonate films. The superior effects of Good-rite™ 3034 are suggested by the lower YI numbers for Good-rite™ 3034 compared to other HALS.

TABLE 1

Photostability of polycarbonate cast films containing HALS.

| Sample | HALS | initial YI | YI at 3286 kJ | YI at 3702 kJ |
|---|---|---|---|---|
| 1 | Control (none) | 0.8 | 4.8 | - (failed) |
| 2 | Tinuvin ® 770 | 0.9 | 2.0 | 2.4 |
| 3 | Tinuvin ® 765 | 0.8 | 2.2 | 2.7 |
| 4 | Sanduvor ® 3058 | 0.8 | 2.5 | 3.3 |
| 5 | GR 3034 | 0.9 | 1.9 | 2.2 |

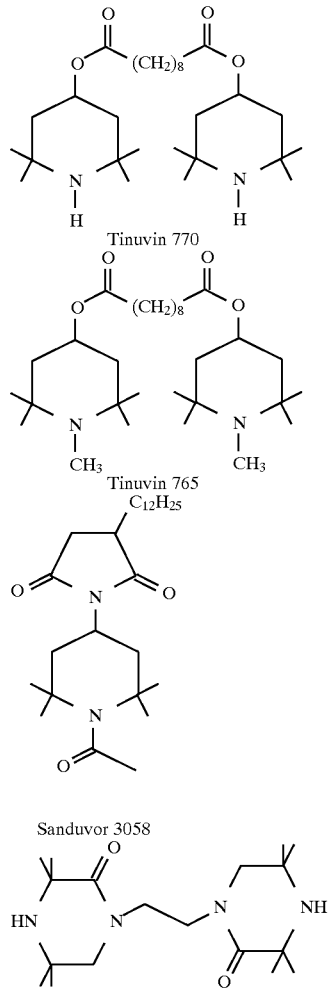

Structures of HALS in Table 1

EXAMPLE 2

Photostability of Injection-Molded Samples Containing HALS

Polycarbonate powder was dried overnight at 60° C. in an oven prior to extrusion. Samples were dry blended with 2.0% by weight of rutile TiO$_2$ and 1.0% by weight of the various HALS.

The blends, in Tables 4, 5a and 5b consisted of BPA-PC and poly(1,4-butylene terephthalate) (PBT) (combined in a 70:30 ratio), rutile TiO$_2$ (2.0% by weight) or carbon black (0.6% by weight added as a 25% master batch in BPA-PC), Good-rite™ 3034 HALS (1.0% by weight) and phosphorous acid (0.08% by weight). Similarly the blends, in Tables 6, 7a and 7b, consisted of BPA-PC and poly(1,4-cyclohexanedimethanol-1,4-cyclohexandicarboxylate) (PCCD) (combined in a 70:30 ratio), rutile TiO$_2$ (2.0% by weight) or carbon black (0.6% by weight added as a 25% master batch in BPA-PC), Good-rite™ 3150 HALS (2.5% by weight) and phosphorous acid (0.05% by weight). In both these blends the phosphorous acid acts as a catalyst quencher to quench the residual polymerization catalyst, that may have been left behind from the synthesis of the polycarbonate or the polyester resin, thereby preventing transesterification. The blends with acrylonitrile-butadiene-styrene consisted of BPA-PC, styrene-acrylonitrile copolymer and butadiene based high rubber graft (combined in a 67:16.5:16.5 ratio), rutile TiO$_2$ (2.0% by weight), HALS (1.0% by weight), Irgaphos-168 (0.3% by weight) and Irganox-1076 (0.3% by weight). Both Irgaphos-168 and Irganox-1076 were added as processing stabilizers.

The formulations were blended by means of a mixer then compounded on a ten barrel Werner & Pfliederer 30 mm co-rotating twin screw extruder. The pelletized formulations were dried overnight in a 60° C. oven then injection molded on a Nissei 160 ton molding press into ⅛" thick plaques under standard conditions. The plaques were weathered under three different conditions. Weathering condition (A) has a 160 min light cycle and a 20 min dark cycle with water spray during the last 15 minutes (all other parameters are the same as in the thin films of Example 1); weathering condition (B) has the same parameters as the thin films in Example 1; weathering condition (C), was conducted in an Atlas Ci35a xenon arc Weather-Ometer® equipped with type-S borosilicate inner and outer filters. The light cycle was 160 minutes long at an irradiance of 0.77 W/m$^2$ at 340 nm, black panel temperature 70° C., dry bulb temperature 45° C., and wet bulb depression 10° C. There was a 20 minute dark cycle with water spray during the last 15 minutes.

The Yellowness Index (YI, ASTM D-1925) of the BPA-PC plaques containing HALS are reported in Tables 2a and 2b. The Goodrite™ piperazinones outperform other HALS in preventing color formation upon weathering as indicated by their lower YI values in Tables 2a and 2b.

TABLE 2a

Photostability of TiO$_2$ pigmented polycarbonate plaques containing HALS: weathering conditions (A)

| HALS | initial YI | YI at 2990 kJ | YI at 3756 kJ |
| --- | --- | --- | --- |
| Control (none) | 4.1 | 16.2 | 26.0 |
| Tinuvin ® 440 | 3.4 | 9.9 | 19.2 |
| Tinuvin ® 770 | 5.8 | 17.9 | 25.7 |
| Tinuvin ® 622 | 4.6 | 10.9 | 20.1 |
| Sanduvor ® 3058 | 5.6 | 12.6 | 23.0 |
| Good-rite ™ 3034 | 4.5 | 8.0 | 13.2 |

TABLE 2b

Photostability of TiO$_2$ pigmented polycarbonate plaques containing HALS: weathering conditions (B)

| HALS | initial YI | YI at 2106 kJ | YI at 2906 kJ |
| --- | --- | --- | --- |
| Control (none) | 5.0 | 10.6 | 23.5 |
| Good-rite ™ 3150 | 4.3 | 6.8 | 14.0 |
| Good-rite ™ 3159 | 5.1 | 6.8 | 14.4 |

The Goodrite™ piperazinones also provided the best gloss retention in TiO$_2$ pigmented BPA-PC plaques as indicated by the higher gloss values in Tables 3a and 3b. Gloss measurements were recorded using a BYK Gardner micro tri gloss meter at a 60° viewing angle. The Goodrite™ piperazinone HALS are also more processable in BPA-PC and provide similar benefit in blends with BPA-PC as described below.

TABLE 3a

Photostability of TiO$_2$ pigmented polycarbonate plaques containing HALS: weathering conditions (A)

| HALS | initial 60° Gloss | 60°Gloss at 2990 kJ | 60°Gloss at 3756 kJ |
| --- | --- | --- | --- |
| Control (none) | 101 | 88 | 24 |
| Tinuvin ® 440 | 101 | 94 | 49 |
| Tinuvin ® 770 | 101 | 91 | 27 |
| Tinuvin ® 622 | 101 | 91 | 48 |
| Sanduvor ® 3058 | 101 | 92 | 33 |
| Goodrite ™ 3034 | 101 | 98 | 77 |

TABLE 3b

Photostability of TiO$_2$ pigmented polycarbonate plaques containing HALS: weathering conditions (B)

| HALS | initial 60° Gloss | 60°Gloss at 2906 kJ | 60°Gloss at 3089 kJ |
| --- | --- | --- | --- |
| Control (none) | 102 | 76 | 28 |
| Goodrite ™ 3150 | 103 | 96 | 74 |
| Goodrite ™ 3159 | 103 | 96 | 74 |

The Yellowness Index of the TiO$_2$ pigmented BPA-PC/PBT blend containing HALS is reported in Table 4, and the gloss values are reported in Table 5a. Gloss values for the BPA-PC/PBT blend containing carbon black and HALS is reported in Table 5b. The color shift in the black samples is not reliably measurable by the Yellowness Index and is, therefore, not reported.

TABLE 4

Photostability of TiO$_2$ pigmented PC/PBT blend plaques containing HALS: weathering conditions (B)

| HALS | initial YI | YI at 808 kJ | YI at 1791 kJ |
| --- | --- | --- | --- |
| Control (none) | 5.8 | 11.8 | 19.8 |
| Goodrite ™ 3034 | 5.0 | 9.2 | 16.3 |

TABLE 5a

Photostability of TiO$_2$ pigmented PC/PBT blend plaques containing HALS: weathering conditions (B)

| HALS | initial 60° Gloss | 60°Gloss at 1608 kJ | 60°Gloss at 1791 kJ |
|---|---|---|---|
| Control (none) | 101 | 63 | 43 |
| Goodrite ™ 3034 | 100 | 72 | 56 |

TABLE 5b

Photostability of carbon black pigmented PC/PBT plaques containing HALS: weathering conditions (B)

| HALS | initial 60° Gloss | 60°Gloss at 1791 kJ | 60°Gloss at 2211 kJ | 60°Gloss at 2607 kJ |
|---|---|---|---|---|
| Control (none) | 101 | 80 | 59 | 39 |
| Good-rite ™ 3034 | 100 | 90 | 72 | 52 |

Data in Tables 4, 5a and 5b indicates that incorporation of Goodrite™ piperazinone enhances photostability of the blends. The enhanced photostability is indicated by higher gloss values and lower YI values.

The Yellowness Index of the TiO$_2$ pigmented BPA-PC/PCCD blend containing HALS is reported in Table 6, and the gloss values are reported in Table 7a. Gloss values for the BPA-PC/PCCD blend containing carbon black and HALS is reported in Table 7b.

TABLE 6

Photostability of TiO$_2$ pigmented PC/PCCD plaques containing HALS: weathering conditions (C)

| HALS | initial YI | YI at 1211 kJ | YJ at 1868 kJ |
|---|---|---|---|
| Control (none) | 9.9 | 18.3 | 27.6 |
| Goodrite ™ 3150 | 8.2 | 12.6 | 18.9 |

TABLE 7a

Photostability of TiO$_2$ pigmented PC/PCCD plaques containing HALS: weathering conditions (C)

| HALS | initial 60° Gloss | 60°Gloss at 1211 kJ | 60°Gloss at 1868 kJ |
|---|---|---|---|
| Control (none) | 101 | 90 | 58 |
| Goodrite ™ 3150 | 99 | 97 | 91 |

TABLE 7b

Photostability of carbon black pigmented PC/PCCD plaques containing HALS: weathering conditions (C)

| HALS | initial 60° Gloss | 60°Gloss at 1974 kJ | 60°Gloss at 2257 kJ |
|---|---|---|---|
| Control (none) | 100 | 52 | 16 |
| Goodrite ™ 3150 | 100 | 72 | 47 |

The Yellowness Index of the TiO$_2$ pigmented BPA-PC/ABS blends containing HALS are reported in Table 8.

TABLE 8

Photostability of TiO$_2$ pigmented PC/ABS plaques containing HALS: weathering conditions (B)

| HALS | initial YI | YI at 1301 kJ | YI at 2230 kJ |
|---|---|---|---|
| Control (none) | 9.2 | 15.0 | 29.7 |
| Good-rite ™ 3034 | 9.7 | 6.1 | 11.9 |

The previous data demonstrates that the benefit observed by adding piperazinone based HALS to BPA-PC is translatable to various blends with BPA-PC. The Good-rite™ piperazinones imparted significantly improved weatherability to TiO$_2$ and carbon pigmented blends of BPA-PC with PBT, PCCD or ABS as evidenced by the higher gloss values and lower YI values relative to the controls.

EXAMPLE 3

Melt Stability

The previous examples demonstrate that Goodrite™ 3034 outperforms other HALS in preventing color formation and loss of gloss in BPA-PC and blends with BPA-PC. However, one must also consider the effect of HALS on the physical properties. The basicity of most HALS results in degradation of polycarbonate during processing and has generally precluded their use in polycarbonate. Several N-alkylated and acylated versions of HALS have been produced in an attempt to overcome this problem. Melt stability of the resins should provide a direct indication of the degree of degradation and consequent effect on physical properties.

Melt stability was measured in a nitrogen purged RDS 7700 rheometer at 300° C. using a frequency of 1 rad/sec on oven dried disks cut from injection molded plaques. Changes in the dynamic rheological properties were measured over a period of 45 min. The results are summarized in Table 10. The initial viscocities of all of the samples containing HALS are lower than the control. Tinuvin® 770 is the most basic of the amines and accordingly results in the most degradation yet even the non-basic acylated amines (Tinuvin® 440 and Sanduvor® 3058) caused significant degradation as evidenced by the drop in viscocity during the course of the test. The formulations containing Goodrite™ 3034, Goodrite™ 3150 1,1',1"-[1,3,5-triazine-2,4,6-triyltris [(cyclohexylimino)]2,1-ethanediyl]]tris{3,3,5,5-tetramethylpiperazinone] and Goodrite™ 3159 1,1',1"-[1,3,5-triazine-2,4,6-triyltris[(cyclohexylimino)-2,1-ethanediyl]]tris-3,3,4,5,5-pentamethylpiperazinone] showed the least change in viscocity during the test.

The combination of processibility and weatherability of Goodrite™ 3034, 3150 and 3159 demonstrates that the piperazinone class is superior to other commercial HALS in polycarbonate.

TABLE 10

Melt Stability of Polycarbonate Containing Hindered Amines

| | Viscocity (poise) | | |
|---|---|---|---|
| HALS | Initial | min | Final |
| Control (none) | 9700 | 9000 | 8900 |
| Tinuvin ® 440 | 6600 | 3900 | 2000 |
| Tinuvin ® 770 | 2300 | 880 | 470 |
| Tinuvin ® 622 | 5400 | 2400 | 980 |

TABLE 10-continued

Melt Stability of Polycarbonate Containing Hindered Amines

| | Viscocity (poise) | | |
|---|---|---|---|
| HALS | Initial | min | Final |
| Sanduvor ® 3058 | 3100 | 2600 | 1500 |
| Goodrite ™ 3034 | 6300 | 5400 | 5200 |
| Goodrite ™ 3150 | 6700 | 5200 | 4600 |
| Goodrite ™ 3159 | 7800 | 5600 | 4800 |

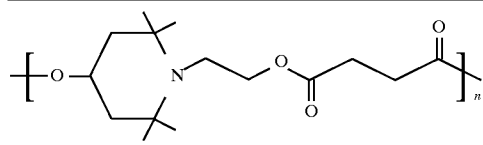

Tinuvin ® 622

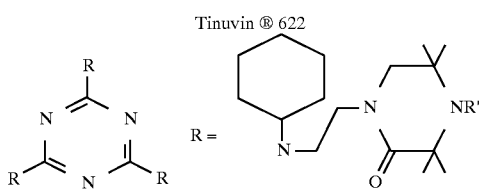

GR 3150: R' = H;  GR 3159: R' = CH₃

We claim:

1. A composition comprising:
   (a) a polycarbonate; and
   (b) a piperazinone based HALS selected from:

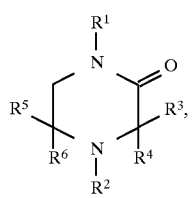 Formula I

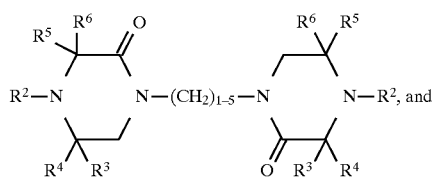 Formula III

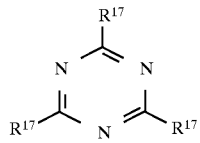 Formula IV wherein:

$R^1$ and $R^2$ are independently $C_{1-24}$ alkyl, hydrogen, $C_{1-12}$ haloalkyl, $C_{2-14}$ alkenyl or unsubstituted $C_{7-14}$ aralkyl;

$R^3$ and $R^4$ are independently $C_{1-18}$ haloalkyl, $C_{1-18}$ alkyl, $C_{5-18}$ cycloalkyl, $C_{2-18}$ alkenyl, or unsubstituted $C_{7-18}$ aralkyl; or $R^3$ and $R^4$, when taken together with the carbon to which they are attached, form a $C_{4-11}$ alicyclic ring;

$R^5$ and $R^6$ are independently $C_{1-18}$ haloalkyl, $C_{1-18}$ alkyl, $C_{2-18}$ alkenyl, or unsubstituted $C_{7-18}$ aralkyl; or $R^5$ and $R^6$ when taken together with the carbon atom to which they are attached, form a $C_{4-11}$ alicyclic ring;

$R^{17}$ is

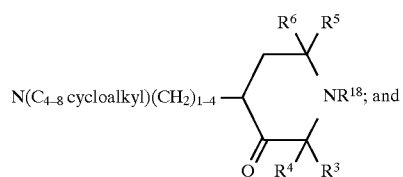

$R^{18}$ is H or $C_{1-4}$ alkyl.

2. A composition comprising:
   (a) a polycarbonate;
   (b) a piperazinone based HALS;
   (c) an additive; and
   (d) a blend stock;

said HALS being selected from:

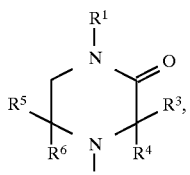 Formula I

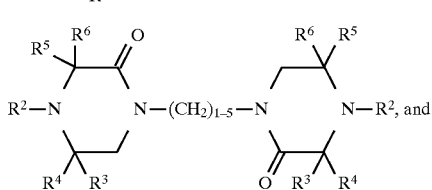 Formula III

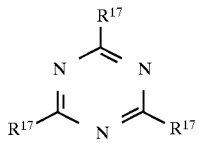 Formula IV wherein:

$R^1$ and $R^2$ are independently $C_{1-24}$ alkyl, hydrogen, $C_{1-12}$ haloalkyl, $C_{2-14}$ alkenyl or unsubstituted $C_{7-14}$ aralkyl;

$R^3$ and $R^4$ are independently $C_{1-18}$ haloalkyl, $C_{1-18}$ alkyl, $C_{5-18}$ cycloalkyl, $C_{2-18}$ alkenyl, or unsubstituted $C_{7-18}$ aralkyl; or $R^3$ and $R^4$, when taken together with the carbon to which they are attached, form a $C_{4-11}$ alicyclic ring;

$R^5$ and $R^6$ are independently $C_{1-18}$ haloalkyl, $C_{1-18}$ alkyl, $C_{2-18}$ alkenyl, or unsubstituted $C_{7-18}$ aralkyl; or $R^5$ and $R^6$ when taken together with the carbon atom to which they are attached, form a $C_{4-11}$ alicyclic ring;

$R^{17}$ is

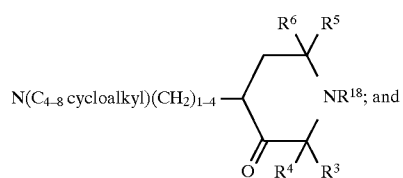

$R^{18}$ is H or $C_{1-4}$ alkyl.

3. A composition of claim 1 wherein:
   (a) the polycarbonate comprises from about 95% to about 99.95% by weight of the total composition; and
   (b) the piperazinone or piperazine dione based HALS comprises from about 5% to about 0.05% by weight of the total composition.

4. A composition of claim 3 wherein HALS comprises from about 0.1% to about 1% by weight of the total composition.

5. A composition of claim 4 wherein, the polycarbonate is BPA polycarbonate.

6. A composition of claim 1 wherein the HALS is a piperazinone represented by:

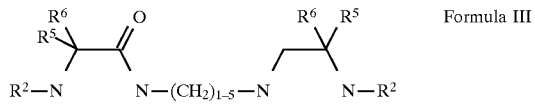

Formula III and

Formula IV wherein, $R^3$, $R^4$, $R^5$, and $R^6$ are each methyl; $R^{17}$ is

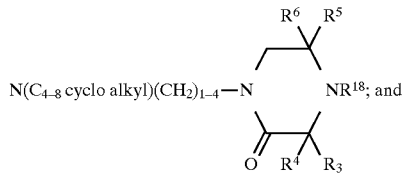

$R^{18}$ is H or $C_{1-2}$ alkyl.

7. A composition of claim 2, wherein:
(a) the polycarbonate comprises from about 38% to about 68% by weight of the total composition;
(b) the piperazinone or piperazine dione based HALS comprises from about 0.05% to about 5% by weight of the total composition;
(c) additives comprise from about 0.01% to about 25% by weight of the total composition; and
(d) the blend stock comprises from about 0% to about 89% by weight of the total composition.

8. A composition of claim 7, wherein HALS comprise from 0.1% to 1%, and the blend stock comprises from about 30% to about 60% by weight of the total composition.

9. A composition of claim 8, wherein, the additives comprise at least one of colorants, stabilizers, impact modifiers, and processing aids.

10. A composition of claim 9, wherein the blend stock comprises at least one of aromatic polyesters, aliphatic polyesters, and styrenic polymers.

11. A composition of claim 10 wherein, the polycarbonate is BPA polycarbonate.

12. A composition of claim 2, wherein the HALS is a piperazinone represented by:

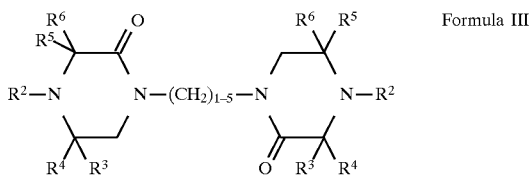

Formula III and

Formula IV wherein, $R^3$, $R^4$, $R^5$, and $R^6$ are each methyl;

$R^{17}$ is

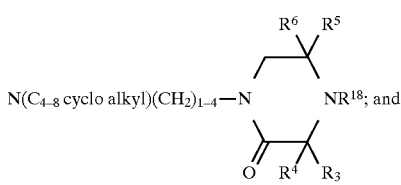

$R^{18}$ is H or $C_{1-2}$ alkyl.

* * * * *